United States Patent [19]

Cartmell et al.

[11] Patent Number: 5,115,801

[45] Date of Patent: May 26, 1992

[54] HYDROGEL BURN DRESSING PRODUCT

[75] Inventors: James V. Cartmell, Centerville; Michael L. Wolf, West Milton; Michael J. Allaire, Dayton; Wayne R. Sturtevant, Centerville, all of Ohio

[73] Assignee: NDM Acquisition Corp., Minneapolis, Minn.

[21] Appl. No.: 517,837

[22] Filed: May 2, 1990

[51] Int. Cl.$^5$ .................. A61F 13/00; A61F 15/00; A61L 15/00

[52] U.S. Cl. ............................. 602/48; 128/888; 604/289; 424/443; 602/56; 602/57; 602/58

[58] Field of Search ............ 128/156, 888; 604/289, 604/307; 424/443, 447

[56] References Cited

U.S. PATENT DOCUMENTS

| | | |
|---|---|---|
| 3,526,224 | 6/1967 | Potts . |
| 3,543,750 | 1/1968 | Meizanis . |
| 3,579,628 | 5/1971 | Gander et al. . |
| 3,648,692 | 3/1972 | Wheeler . |
| 4,061,618 | 12/1977 | Stanley et al. . |
| 4,156,066 | 5/1979 | Gould . |
| 4,156,067 | 5/1979 | Gould . |
| 4,226,232 | 10/1980 | Spence . |
| 4,341,207 | 7/1982 | Steer et al. ................. 128/155 |
| 4,393,048 | 7/1983 | Mason, Jr. et al. . |
| 4,460,369 | 7/1984 | Seymour . |
| 4,517,326 | 5/1985 | Cordts et al. . |
| 4,538,603 | 9/1985 | Pawelchak et al. . |
| 4,595,001 | 6/1987 | Potter et al. . |
| 4,657,006 | 4/1987 | Rawlings et al. . |
| 4,669,458 | 6/1987 | Abraham et al. . |
| 4,704,119 | 11/1987 | Shaw et al. . |
| 4,743,249 | 5/1988 | Loveland . |
| 4,747,401 | 5/1988 | Potter et al. . |
| 4,753,232 | 1/1988 | Ward . |
| 4,759,354 | 7/1988 | Quarfoot ...................... 128/155 |
| 4,907,579 | 3/1990 | Kum ............................. 128/888 |
| 4,909,244 | 3/1990 | Quarfoot et al. . |
| 4,977,892 | 12/1990 | Ewall ........................... 128/156 |
| 4,979,946 | 12/1990 | Gilman ......................... 604/307 |
| 5,006,342 | 4/1991 | Cleary et al. ................. 424/447 |

FOREIGN PATENT DOCUMENTS

| | | |
|---|---|---|
| 0174803A3 | 3/1986 | European Pat. Off. . |
| 2347299 | 4/1975 | Fed. Rep. of Germany . |
| WO88/01877 | 3/1988 | PCT Int'l Appl. . |
| 2198441A | 6/1988 | United Kingdom . |

OTHER PUBLICATIONS

Abstract of German patent DE2347299 published Apr. 10, 1975 (in English).

Smith & Nephew advertisement describing a Flexigrid Application System, copyright 1990, 10,000 copies distributed.

Smith & Nephew Abstract of lecture presented at Advanced Wound Care Symposium, Mar. 12, 1990.

Primary Examiner—Randall L. Green
Assistant Examiner—Paul Prebilic
Attorney, Agent, or Firm—Killworth, Gottman, Hagan & Schaeff

[57] ABSTRACT

A flexible burn dressing product contains a hydrogel material in a gel-like phase. The burn dressing product is comprised of several layers including a burn dressing and a release layer. The burn dressing is comprised of a bacterial barrier layer coated with a bonding layer, a reticulated layer impregnated with a hydrogel material, and a hydrogel material layer. A dimensionally stable backing member may also be adhesively attached to the bacterial barrier layer to help the burn dressing maintain its shape until it is applied to a patient. When the burn dressing product is to be applied to a burn site, the release layer is removed to expose the hydrogel material layer. The remaining layers of the burn dressing product are then applied to the burn site, with the hydrogel material layer directly contacting the burn. Once these layers are in place, the dimensionally stable backing member is removed.

5 Claims, 4 Drawing Sheets

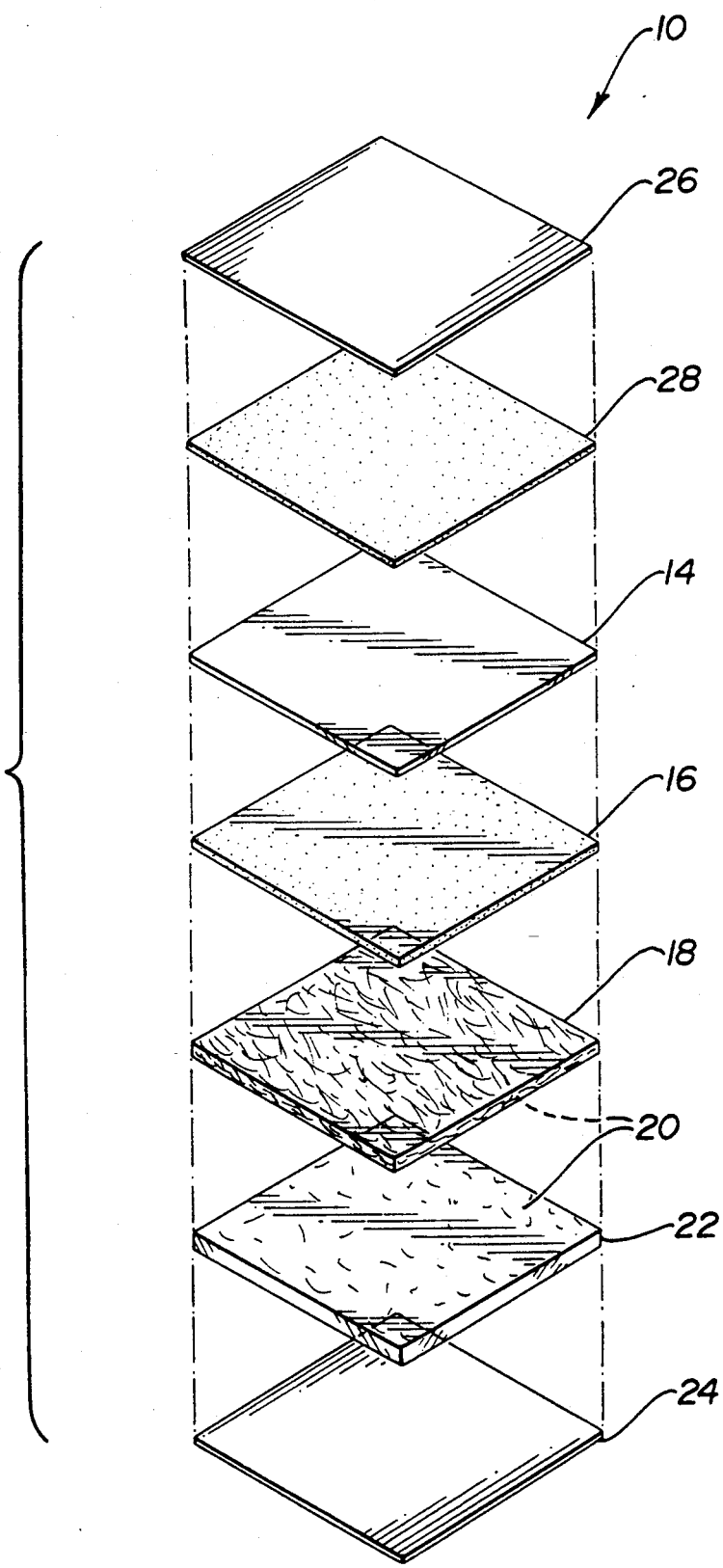

HYDROGEL BURN DRESSING PRODUCT

BACKGROUND OF THE INVENTION

This invention relates to burn dressings and, more particularly, to a flexible burn dressing product containing a hydrogel substance particularly useful in the active therapy of thermal, chemical, electrical, and similar wounds conventionally classified as "burns."

Burn injuries require a unique combination of therapy and dressing because the physiologic functions of the skin are absent or, at best, materially impaired. Body fluids and their essential components are continuously lost. The natural barrier characteristics normally provided by one's skin, of preventing invasion of harmful micro-organisms and other noxious agents, are no longer functional. Potentially fatal infections are a continuous serious threat to burn patients. The debris reservoir of necrotic tissue saturated with seeping wound exudate remains on the wound site, harboring and nourishing agents of infection whose presence and by-products interfere with the regeneration of viable, functioning, epithelial tissue having skin organ properties.

The basic tenets of therapy required to treat burns are specifically directed toward providing and improving the impaired physiologic functions of the skin. Of initial concern is the removal of the necrotic products of injury. Also of great importance is providing a barrier to bacterial invasion from the environment while controlling the contamination already present. Finally, burn therapy is directed toward stemming the loss of vital body fluids.

Burn injuries and the like have been treated at various stages by application of sterile coverings in the form of pastes or creams, gauze wrappings, natural and synthetic membranes, films, or sponges. Except in the case of skin grafting, the approach has been to prevent adhesion of the covering materials to the wound site while encouraging adhesion of the burn exudate to the covering materials.

One existing burn exudate absorption method is to apply a polyurethane polymer composition to the burn site. As disclosed in Gould, U.S. Pat. No. 4,156,066, and Gould, U.S. Pat. No. 4,156,067, issued May 22, 1979, a polyurethane polyether resin may be applied to a burn as a powder. However, Powder tends to attract fluids from the burn wound and deteriorates as the wound fluids are absorbed, resulting in lumping and uneven application. Additionally, such deteriorated lumps are difficult to remove from a burn site without damaging new cell tissue at the burn site.

A burn dressing which attempts to minimize fluid loss from the burn site is disclosed in U.S. Pat. No. 3,648,692, issued to Wheeler on Mar. 14, 1972. The Wheeler burn dressing discloses an open cell foam material which can be applied directly to a burn wound site. However, while it is desirable to stem the loss of vital body fluids from the already weakened patient, the Wheeler burn dressing eliminates or minimizes the loss of all fluids, even fluids contaminated with necrotic tissue, from the burn site. Also, new cell tissue forming at the burn site may adhere to the sponge-like material, making it difficult to remove the burn dressing from the burn site without damaging new cell tissue. Consequently, the Wheeler burn dressing serves merely as a sedentary covering for allowing the burn to heal, rather than actively expediting the healing.

Aqueous moisture absorbing materials, such as a polyethylene glycol liquid curing agent as disclosed in Spence, U.S. Pat. No. 4,226,232, issued Oct. 7, 1980, are easier to remove from the wound site, but cannot be sterilized by irradiation due to the formation of free radicals within the aqueous material. Another aqueous absorbing material used to absorb wound exudate, hydrophilic polymer, is disclosed in Rawlings et al, U.S. Pat. No. 4,657,006, issued Apr. 14, 1987. In the Rawlings et al reference, a wound dressing is described which comprises a hydrophilic polymer having moisture vapor permeability characteristics. A problem with the Rawlings et al wound dressing is that the wound exudate absorbed by the hydrophilic polymer hardens the polymer, allowing pockets to develop between the polymer and the wound, providing an excellent environment for bacteria proliferation.

Known aqueous moisture absorbing wound dressing systems have additional problems, in that the aqueous material is generally contained in the center portion of a wound dressing, with a bulky adhesive border, such as a foam border. Problems with such borders include decreased comfort, conformity and adhesion as well as the existence of a "lifting edge" that can catch on clothes or bed sheets, thereby exposing the wound to bacteria and infection. In addition, burn sites typically have very little healthy skin to which such a dressing may be adhered.

An existing method of overcoming the problems associated with bulky wound dressings is disclosed in Potts, U.S. Pat. No. 3,526,224 issued Sep. 1, 1970. The Potts reference discloses a wound dressing comprised of an elastomeric polyurethane film which acts as a second skin during the wound healing process. One problem with the Potts wound dressing, however, is that the "second skin" requires surgery to remove it after the wound has healed.

Hence, it would be desirable to provide a burn dressing which eliminates or minimizes vital and healthy fluid loss from a burn site while simultaneously removing contaminated or infected wound fluids. It would also be desirable to provide a burn dressing product which could be readily available for application to a burn wound. It would further be desirable to provide such a burn dressing which contains wound debridement characteristics but does not adhere to the burn site, thereby providing means to expedite healing. In addition, it would be desirable to provide a burn dressing which could be removed neatly and, more importantly, without adhering to the new cell tissue forming at the burn site. Finally, it would be desirable to provide such a burn dressing product which could be comfortably applied to any area on a body.

SUMMARY OF THE INVENTION

The present invention meets these needs by providing a thin-film burn dressing containing an aqueous hydrogel material, partially impregnated in a reticulated layer which may be of any suitable material including foam, scrim or non-woven material. The present invention also provides a method of manufacture and application of a burn dressing product which includes the burn dressing. The burn dressing product herein can be manufactured to any desirable size to provide a wound debridement dressing for any size burn site. The burn dressing herein is adhesive only to the extent that exuding wound fluids are absorbed, and non-adhesive upon removal from the burn site.

The burn dressing product of the present invention comprises a burn dressing which includes a bacterial barrier layer having a first side and a second side; a bonding layer, the bonding agent positioned on the first side of the bacterial barrier layer; a reticulated layer having a first side and a second side, the reticulated layer being impregnated with a hydrogel material; and a hydrogel material layer on the first side of the impregnated layer. The burn dressing product further comprises a release liner overlying the hydrogel material layer and secured to the first side of the impregnated layer by means of the hydrogel material layer.

A further embodiment of the burn dressing product may include a dimensionally stable backing member having an adhesive layer, the backing member secured to the second side of the bacterial barrier layer by means of the adhesive layer. In a preferred embodiment, the bacterial barrier layer comprises a polyurethane material, the release liner is silicone coated, and the bonding layer comprises a medical grade acrylic adhesive. However, the bonding layer may be any suitable bonding means such as adhesive or flame bonding. Also, the hydrogel material of the burn dressing product comprises from about 15% to about 30% by weight of a polyhedric alcohol, from about 8% to about 14% by weight of an isophorone diisocyanate terminated prepolymer, from about 5% to about 10% by weight of a polyethylene oxide based diamine, up to about 1% by weight of a salt, and the balance water.

In a preferred embodiment of this burn dressing product, the hydrogel comprises 17% by weight of the polyhydric alcohol, 12% by weight of the isophorone diisocyanate terminated prepolymer, 9% by weight of the polyethylene oxide based diamine, 1% by weight of the salt, and the balance water.

The present invention also provides a method of manufacturing the burn dressing product. Initially, a release liner, a reticulated layer such as foam, scrim, or non-woven material, and a bacterial barrier layer are provided, each layer having a first side and a second side. The first side of the bacterial barrier layer is then coated with a bonding layer, after which the second side of the reticulated layer is bonded to the first side of the release liner, wherein the bonding layer is located between the reticulated layer and the release liner. The reticulated layer is impregnated with a hydrogel material, the hydrogel material forming a smooth hydrogel layer on the first side of the impregnated layer. The second side of the release liner is applied to the first side of the impregnated layer, wherein the smooth hydrogel material layer is located between the impregnated layer and the release liner.

Since the impregnated layer and aqueous hydrogel are extremely flexible and pliable, the method of manufacturing the burn dressing product may further include the step of providing a dimensionally stable backing member to maintain the burn dressing in its desired shape until the burn dressing product is applied to a burn site. The dimensionally stable backing member is applied to the second side of the bacterial barrier layer, wherein an adhesive layer is located between the second side of the bacterial barrier layer and the dimensionally stable backing member. In a preferred embodiment of the invention, the bonding layer preferably has stronger bonding qualities than the adhesive layer so as to allow removal of the dimensionally stable backing member from the bacterial barrier layer after application of the burn dressing product to the burn, while maintaining adhesion between the hydrogel material layer and the skin of a patient.

Finally, the present invention provides a method of application of the burn dressing product described above. When the burn dressing product is to be applied to a burn site, the release liner is partially removed to expose the hydrogel material layer so the hydrogel can contact the burn site. The burn dressing product is then applied directly over the burn site in a rolling motion, while continuing to remove the release liner until the release liner is completely removed and the burn dressing completely covers the burn site.

Directly contacting the burn is the hydrogel material layer, where it creates a bio-compatible, bacterial protective, fluid absorbing, cushioned skin-like media to facilitate the healing process. Once the burn dressing product has been placed on the burn site, then the dimensionally stable backing member can be removed. The result is a burn dressing containing a bio-compatible, non-irritating, fluid absorbing, skin-like media hydrogel material. Conformity and, more importantly, bacterial protection is improved since there is no "lifting edge" to catch on clothing or bed sheets.

The hydrogel material has healing and absorbing qualities and is preferably a saline solution in an aqueous gel phase, which is impregnable within the reticulated layer. The gel consistency of the hydrogel material creates a bond between the burn dressing and the burn site without creating an actual adhesive attachment that would damage new cell tissue upon removal. An advantage of the gel hydrogel is that it will absorb exudating burn wound fluids. Additionally, it permits clean and neat removal of the burn dressing when the burn heals or the dressing is changed. Finally, since the hydrogel material is transparent, it is possible to inspect the burn site without removing the burn dressing, provided the other layers of the burn dressing product are also transparent.

It is an object of the present invention to provide a burn dressing product containing an aqueous hydrogel substance which is particularly advantageous when used to dress burn sites, by providing a skin-like media which is bio-compatible, non-irritating, fluid absorbing, and bacterial protective; to provide a burn dressing which is more flexible and less bulky than existing dressings; to provide a burn dressing which will not adhere to new cell tissue when it is removed; and to provide a burn dressing product with the above features that is readily available for application to a burn site.

Other objects and advantages of the invention will be apparent from the following description, the accompanying drawings, and the appended claims.

BRIEF DESCRIPTION OF THE DRAWINGS

FIG. 3 is an exploded view, illustrating the layers which form the preferred embodiment of the burn dressing product.

DETAILED DESCRIPTION OF THE INVENTION

The present invention relates to a burn dressing product for application to a burn site. The burn dressing product is comprised of a burn dressing and a release liner. The invention also includes a method of manufacture and a method of application for the disclosed burn dressing product.

Figure 1:
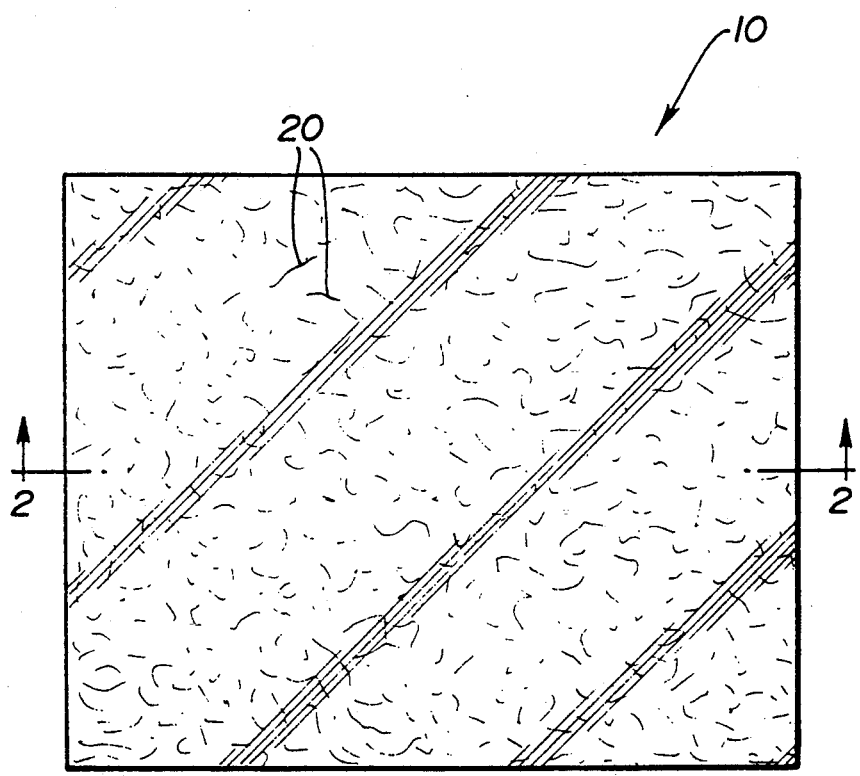
FIG. 1 is a plan view of the burn dressing product.

The burn dressing product 10 of the present invention is illustrated in FIGS. 1, 2A, 2B, and 3. Although the burn dressing product 10 is shown in FIG. 1 as having a rectangular shape, it may be any of a variety of desirable shapes. The burn dressing product 10 is composed of several layers including a wound dressing 12, as illustrated by the cross-sectional view of FIG. 2A and the exploded view of FIG. 3.

Figure 2A:
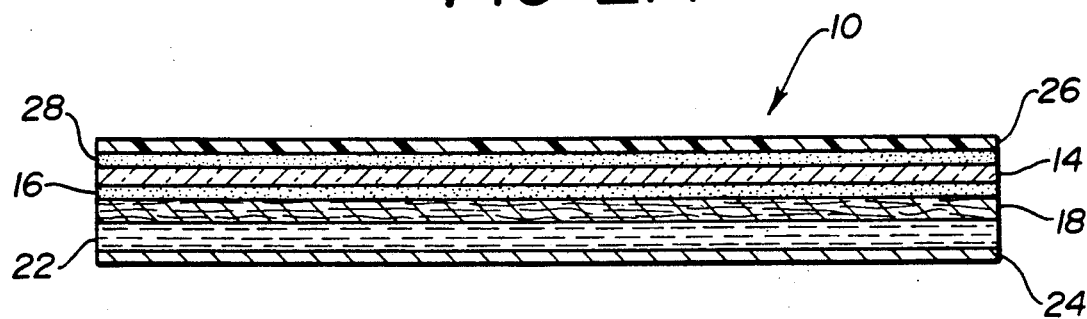
FIGS. 2A and 2B are cross-sectional views of the burn dressing product and the burn dressing, respectively, of FIG. 1 taken along line 2—2.
Figure 2B:
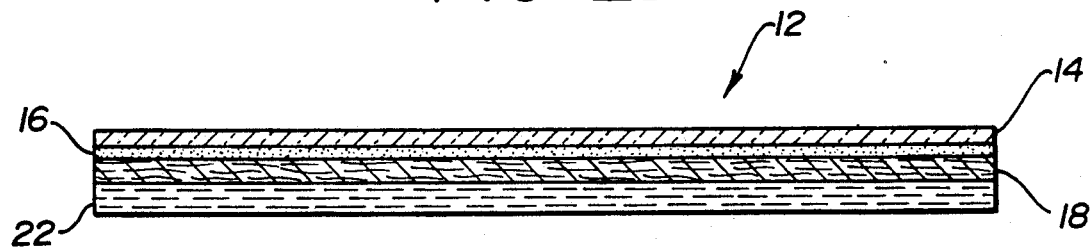

Referring now to FIG. 2A, the burn dressing product 10 is illustrated in cross-section, taken along line 2—2 of FIG. 1. The burn dressing product 10 includes a bacterial barrier layer 14, preferably of polyurethane. The bacterial barrier layer 14 has a first side and a second side, the first side being coated with a bonding agent to form bonding layer 16. The bonding layer 16 preferably comprises a medical grade acrylic adhesive, but may be any suitable bonding means including flame bonding. Attached to the bacterial barrier layer 14 via the bonding layer 16 is a reticulated layer 18, which layer 18 may be any suitable reinforcing material such as reticulated foam, scrim, or non-woven material, the layer 18 having a first side and a second side. The reticulated layer 18 is preferably absorbent enough to permit a hydrogel material 20 to be impregnated in the reticulated layer 18. A hydrogel material layer 22 is then secured by bonding or other means to the first side of the impregnated layer 18. Finally, a release liner 24, preferably silicone coated, overlies the hydrogel material layer 22 and is secured to the first side of the impregnated layer 18 by means of the hydrogel material layer 22. The bacterial barrier layer 14, the bonding layer 16, the impregnated layer 18, and the hydrogel material layer 22 comprise the wound dressing 12, as illustrated in FIG. 2B.

The combination of the impregnated layer 18 and the hydrogel material layer 22 is particularly advantageous for use on burn wounds. The impregnated layer 18 provides a cushion to protect the burn site from external trauma, but does not directly contact the burn site. Instead, to avoid having new cell tissue adhere to the impregnated layer 18, the smooth, gel hydrogel material layer 22 directly contacts the wound.

In a further embodiment, the burn dressing product 10 may include a dimensionally stable backing member 26, illustrated in FIGS. 2A and 3. The backing member 26 is secured to the second side of the bacterial barrier layer 14 by means of an adhesive layer 28. Also in a preferred embodiment of the invention, the bonding layer 16, located between the bacterial barrier layer 14 and the impregnated layer 18, has stronger bonding qualities than the adhesive layer 28, located between the bacterial barrier layer 14 and the dimensionally stable backing member 26. Such a construction allows removal of the dimensionally stable backing member 26 from the burn dressing 12 while maintaining the adhesion between the bacterial barrier layer 14 and the impregnated layer 18.

The present invention provides a method of manufacturing the wound dressing product 10. In the manufacturing method of the present invention, the release liner 24, the impregnated layer 18, and the bacterial barrier layer 14 are provided, each having a first side and a second side. Since the impregnated layer and aqueous hydrogel are pliable, the method of manufacturing the burn dressing product 10 may further include the step of providing the dimensionally stable backing member 26, having a first side and a second side, to maintain the burn dressing 12 in its desired shape until the burn dressing product 10 is applied to a burn site. The first side of the bacterial barrier layer 14 is coated with the bonding agent of the bonding layer 16 and the first side of the dimensionally stable backing member 26 is coated with the adhesive layer 28, which is illustrated in FIGS. 2A and 3. The second side of the bacterial barrier layer 14, if used in the manufacture of the burn dressing, is then laminated to the first side of the dimensionally stable backing member 26, wherein the adhesive layer 28 is located between the bacterial barrier layer 14 and the dimensionally stable backing member 26, as can be seen in FIG. 2A.

Once the layers of the burn dressing product 10 are manufactured, the reticulated layer 18 is impregnated with a clear, gel aqueous material 20, preferably hydrogel, which forms a smooth hydrogel material layer 22 on the first side of the impregnated layer 18. After the hydrogel material 20 has been impregnated in the reticulated layer 18, the second side of the release liner 24 is applied to the first side of the hydrogel material layer 22.

The hydrogel material 20 is formed from about 15% to about 30% by weight of a polyhedric alcohol selected from a group consisting of polypropylene glycol, polyethylene glycol and glycerine, from about 8% to about 14% by weight isophorone diisocyanate terminated prepolymer, from about 5% to about 10% by weight polyethylene oxide based diamine, up to about 1% by weight of a salt, and the remaining percentage being water. In the preferred embodiment of the present invention, the hydrogel material 20 is formed 17% polypropylene glycol, 12% isophorone diisocyanate terminated prepolymer, 9% polyethylene oxide based diamine, 1% salt, and 61% water. The resulting urea hydrogel material 20 and the hydrogel material layer 22 provide a bio-compatible, non-irritating, fluid absorbing, bacterial protective, cushioning, skin-like media over the burn site. An additional advantage of the hydrogel is that the hydrogel material 20 and the hydrogel material layer 22 are transparent, making it possible to inspect the burn site without removing the burn dressing, provided the bacterial barrier layer 14, the bonding layer 16, and the impregnated layer 18 are all transparent as well.

Figure 4A:
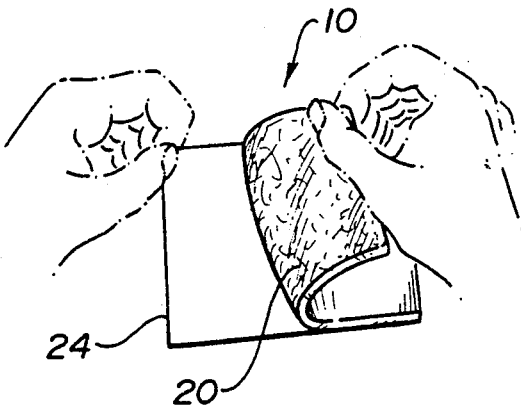
FIGS. 4A through 4D illustrate the preferred method of application of the burn dressing product of the present invention.
Figure 4B:
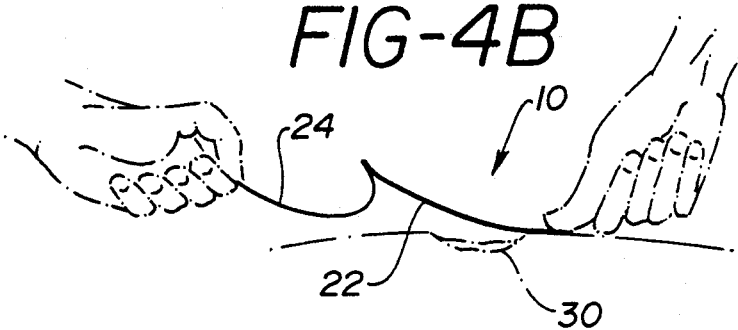
Figure 4C:
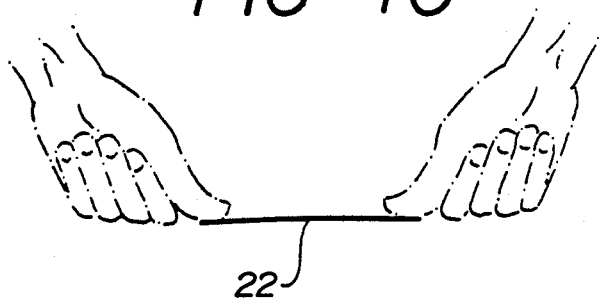
Figure 4D:
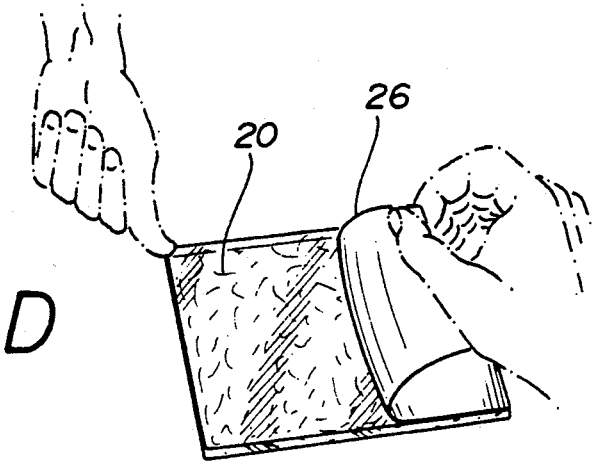

Referring now to FIGS. 4A–4D, a preferred method of application of the burn dressing product 10 is illustrated in sequence. FIG. 4A illustrates how the release liner 24 can be gripped by the person applying the burn dressing product 10, to begin removal of the release liner 24 and expose the hydrogel material layer 22 before the burn dressing product 10 is applied to the burn site. In FIG. 4B, the burn dressing product 10 has been flipped over so the hydrogel material layer 22 can contact the burn site 30. The release liner 24 continues to be removed in a rolling motion as the hydrogel material layer 22 is placed over the burn site 30. Once the release liner 24 has been completely removed and the remaining layers of the burn dressing product 10 are properly situated over the burn site 30, the burn dressing product 10 is secured to the burn site 30 by gently pressing into place the burn dressing product 10, as illustrated in FIG. 4C. Finally, in one embodiment, as shown in FIG. 4D, if the dimensionally stable backing member 26 is used, it is peeled away from the bacterial barrier layer 14, to leave only the burn dressing 12 on the burn site 30.

Once the dimensionally stable backing member 26 has been completely removed, or if the dimensionally stable backing member is not used in the embodiment, only the bacterial barrier layer 14, the impregnated layer 18, and the hydrogel material layer 22, remain on the burn site 30. The result is a burn dressing 12 containing a burn healing hydrogel material layer 22 which gently contacts the burn site 30.

The burn dressing product 10 of the present invention is particularly advantageous for use on exuding burns. In particular, a special feature of the hydrogel material layer 22 is that it retains its gel integrity even upon removal of the burn dressing 12 from a burn site. The hydrogel material layer 22 does not leave debris in the burn when the burn dressing is removed, nor does it adhere to the burn site. The benefit of this feature is that the hydrogel material layer 22 exhibits a capability of non-traumatically releasing from the burn when the burn dressing 12 is removed, so as not to destroy new cell tissue forming at the burn site. Thus, healing is not inhibited by removal of the dressing 12.

Having described the invention in detail and by reference to preferred embodiments thereof, it will be apparent that modifications and variations are possible without departing from the scope of the invention which is defined in the appended claims.

What is claimed is:

1. A burn dressing product for a burn, comprising:
    a burn dressing including
        a bacterial barrier layer having a first side and a second side,
        a bonding layer coated on said first side of said bacterial barrier layer,
        a reticulated layer being sufficiently absorbent to be impregnated with a polyurethane hydrogel material, said reticulated layer being selected from the group consisting of foams, scrim and non-woven materials, said reticulated layer having a first side and a second side, wherein said second side of said reticulated layer is secured to said bacterial barrier layer by means of said bonding layer, and
        a polyurethane hydrogel material layer on said first side of said impregnated reticulated layer; and
    a release liner overlying said hydrogel material layer and secured to said first side of said reticulated layer by means of said hydrogel material layer.

2. A burn dressing product as claimed in claim 1 further including a dimensionally stable backing member having an adhesive layer, said backing member secured to said second side of said bacterial barrier layer by means of said adhesive layer.

3. A burn dressing product as claimed in claim 1 wherein said bacterial barrier layer comprises a polyurethane material.

4. A burn dressing product for a burn, comprising:
    a burn dressing including
        a bacterial barrier layer having a first side and a second side;
        a bonding layer coated on said first side of said bacterial barrier layer;
        a reticulated layer impregnated with a hydrogel material and having a first side and a second side, said second side of said reticulated layer being secured to said bacterial barrier layer by means of said bonding layer;
        a hydrogel material layer on said first side of said impregnated reticulated layer wherein said hydrogel material is formed from about 15% to about 30% by weight of a polyhydric alcohol selected from a group consisting of polypropylene glycol, polyethylene glycol and glycerine, from about 8% to about 14% by weight of an isophorone diisocyanate terminated prepolymer, from about 5% to about 10% by weight of a polyethylene oxide based diamine, up to about 1% by weight of a salt, and the balance water; and
    a release liner overlying said hydrogel material layer and secured to said first side of said reticulated layer by means of said hydrogel material layer.

5. A burn dressing product for a burn, comprising:
    a burn dressing including
        a bacterial barrier layer having a first side and a second side;
        a bonding layer coated on said first side of said bacterial barrier layer;
        a reticulated layer impregnated with a hydrogel material and having a first side and a second side, said second side of said reticulated layer being secured to said bacterial barrier layer by means of said bonding layer;
        a hydrogel material layer on said first side of said impregnated reticulated layer wherein aid hydrogel material is formed from 17% by weight of a polypropylene glycol, 12% by weight of an isophorone diisocyanate terminated prepolymer, 9% by weight of an polyethylene oxide based diamine, 1% by weight of a salt, and the balance water; and
    a release liner overlying said hydrogel material layer and secured to said first side of said reticulated layer by means of said hydrogel material layer.

* * * * *